United States Patent [19]

Caspar et al.

[11] Patent Number: 4,503,848
[45] Date of Patent: Mar. 12, 1985

[54] OSTEOSYNTHESIS PLATE

[75] Inventors: Wolfhard Caspar, Bad Homburg; Theodor Lutze, Dürbheim, both of Fed. Rep. of Germany

[73] Assignee: Aesculap-Werke Aktiengesellschaft, Tuttlingen, Fed. Rep. of Germany

[21] Appl. No.: 361,879

[22] Filed: Mar. 25, 1982

[30] Foreign Application Priority Data

Apr. 8, 1981 [DE] Fed. Rep. of Germany ....... 3114136

[51] Int. Cl.$^3$ ................................ A61F 5/04
[52] U.S. Cl. ................................ 128/92 D
[58] Field of Search .......... 128/92 D, 92 BA, 92 BB, 128/92 G; 248/558; 52/726, 514; 403/405

[56] References Cited

U.S. PATENT DOCUMENTS 2,780,223 2/1957 Haggland ................................ 128/92
3,779,240 12/1973 Kondo ................................ 128/92 D
4,219,015 8/1980 Steinemann ................................ 128/92 D

FOREIGN PATENT DOCUMENTS 622218 6/1961 Canada ................................ 403/405
1429633 3/1976 United Kingdom ........... 128/92 BA Primary Examiner—C. Fred Rosenbaum
Assistant Examiner—J. L. Kruter
Attorney, Agent, or Firm—Kenway & Jenney

[57] ABSTRACT

To make possible the effective immobilization of pieces of bone with an osteosynthesis plate, the proposal is made that the longitudinal edges of the osteosynthesis plate diverge in the manner of a trapezoid, that the osteosynthesis plate be provided with two adjacent rows of slots for its screws, and that the orientations of the longitudinal axes of the slots in both rows diverge in the same directions as the diverging longitudinal edges of the osteosynthesis plate itself.

2 Claims, 2 Drawing Figures

OSTEOSYNTHESIS PLATE

BACKGROUND OF THE INVENTION

The invention concerns an osteosynthesis plate for mutually immobilizing several pieces of bone by means of screws that may be screwed into the pieces of bone through openings in the osteosynthesis plate, pressing the osteosynthesis plate, which is bent across its longitudinal direction, with its concave surface firmly against the pieces of bone.

Skeletal parts in human and animal bodies—in particular, articulated segments—are often immobilized relative to one another so that the healing process, for example, after a fracture, cannot be unfavorably influenced by movement. It is scientifically accepted that absolute immobilization is the most important prerequisite for the primary healing of bone injuries. Healing in an improper position, with its attendant disadvantageous consequences, may also be avoided by means of this immobilization.

For this purpose elongated, rectangularly-shaped osteosynthesis plates are known that have a concave curvature so that they may be set against the bones. These plates contain a number of holes, through which are placed screws with which the plates are screwed firmly against the pieces of bone to be immobilized. With known osteosynthesis plates, the holes are designed in such a manner as to permit the screws to be turned through them with the necessary play, and the screw heads make solid contact with a countersinking in the surface of the plate. Osteosynthetis plates exist in which the holes have a drop shape and may therefore be used with screws of different diameters. With another type of known plate, the screw openings are machined in such a way that when a screw is put in at an angle, its head rests against the plate and automatically locks it into position.

Osteosynthesis plates are also known that have a T-shape, or a double T-shape, in which the holes for the screws are arranged next to each other in a row and are formed precisely round in accordance with the diameter of the screws.

It is the task of this invention to further develop an osteosynthesis plate of the known type in such a manner that exceptionally effective immobilization of the pieces of bone may be achieved with its use.

SUMMARY OF THE INVENTION

This problem is solved according to the invention with an osteosynthesis plate of the type described initially by making the longitudinal edges of the osteosynthesis plate divergent in the manner of a trapezoid, providing the osteosynthesis plate with two adjacent rows of elongated holes, or slots, for its screws, and making the orientation of the longitudinal axes of the slots in both of these rows divergent like the longitudinal edges of the osteosynthesis plate itself. As a result of the trapezoidally diverging side edges of the osteosynthesis plate, it provides a particularly good fit for pieces of bone that are likewise trapezoidal or divergent in shape. In this way the contact surfaces by which the coefficients of friction are determined for the pieces of bone to be connected, may be made proportionally equal in size.

The design of the screw holes as slots permits a particularly large range of variation with respect to screw positioning, providing latitude for taking into account the anatomical conditions of a given case. As a result of the fact that the slots in the two rows are arranged in diverging directions, exceptionally secure fixation of the osteosynthesis plate in its longitudinal direction results, since the screws when firmly installed offer considerable resistance to displacement of the plate in its longitudinal direction as a result of the varying spacing of the slots.

As a result of the use of two adjacent rows of holes, the screws may be installed with their points on the midpoint presented by the concave curvature, so that all the forces may be withstood that occur in a perpendicular direction from the center of the plate.

According to an advantageous elaboration of the invention, provision is made for the length of the slots to increase from the narrow end to the wide end of the osteosynthesis plate.

It is also advantageous if each of the slots lies in a row, and the common longitudinal axis of all slots in each row runs parallel to the adjacent edge of the osteosynthesis plate.

The following description of a preferred execution of the invention is provided in connection with the illustration for further explanation. Shown are:

DESCRIPTION OF THE PREFERRED EMBODIMENTS

Figure 1:
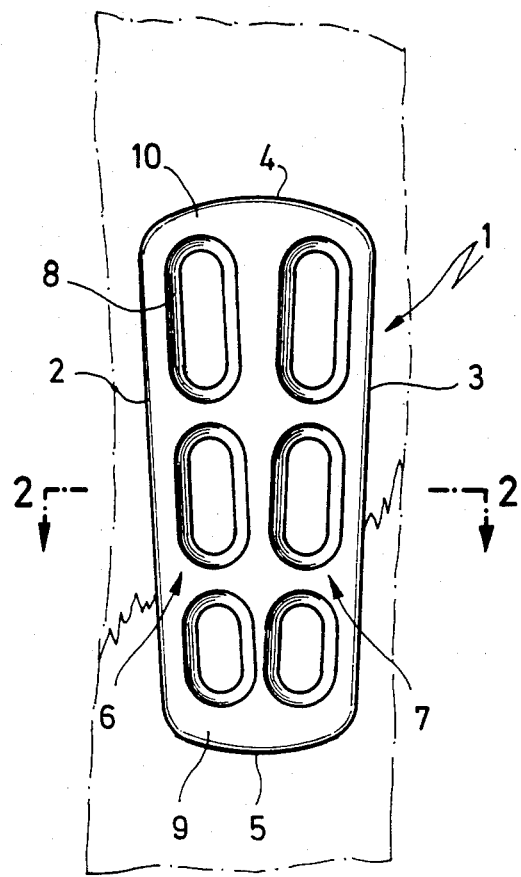
FIG. 1 a top view of an osteosynthesis plate according to the invention.

The osteosynthesis plate 1 represented in the illustration has an essentially trapezoidal outer contour, its two elongated side edges 2 and 3 diverging. These straight, elongated side edges 2 and 3 are connected to each other by rounded upper and lower edges 4 and 5.

Extending parallel to each side edge is a row of slots 6 and 7, each of which contains several slots whose longitudinal axes conicide and run parallel to their adjacent side edge.

Each of the slots is provided with bevels 8 (FIG. 2), so that the correspondingly shaped countersunk ends of the bone screws are admitted completely into the thickness of the plate.

The length of the slots increases from the narrow end 9 of the osteosynthesis plate to its wide end 10.

Figure 2:
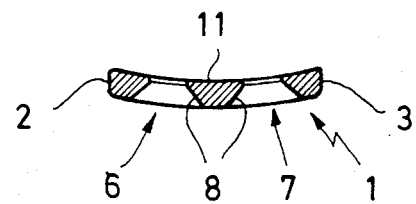
FIG. 2 a sectional line along line 2—2 in FIG. 1.

As may be seen from FIG. 2, the osteosynthesis plate is curved across its longitudinal direction so that it contacts the bone pieces to be immobilized with its concave side 11, and is pressed firmly against the pieces of bone by the screws (not represented in the illustration) when they are installed.

We claim:

1. Osteosynthesis plate for mutually immobilizing several pieces of bone by means of screws that may be screwed into the pieces of bone through openings in the osteosynthesis plate that has longitudinal edges and is curved in the direction transverse to its longitudinal axes to form a concave inner surface adjacent said bone, said screws pressing the concave surface of the ostoesynthesis plate firmly against the pieces of bone, wherein the improvement comprises the longitudinal edges (2, 3) of the osteosynthesis plate (1) diverging in the manner of a trapezoid, and wherein said openings comprise two adjacent rows (6, 7) of elongated slots formed in said osteosynthesis plate to receive said screws, and the orientations of the longitudinal axes of the slots in the two rows (6, 7) diverging in the same direction as the diverging longitudinal edge of the plate the length of its slots increasing from the narrow end (9) of the osteosynthesis plate (1) to its wide end (10).

2. Osteosynthesis plate in accordance with claim 1, distinguished by the fact that each of the slots lies in a row, and the longitudinal axis of all the slots in this row for each row runs parallel to the longitudinal edge (2, 3) of the osteosynthesis plate (1) itself.

* * * * *